(12) United States Patent
Teng

(10) Patent No.: US 7,048,954 B2
(45) Date of Patent: May 23, 2006

(54) METHOD FOR PREPARING AN EXTRACT OF GINKGO BILOBA LEAVES HIGHLY ENRICHED IN ACTIVE PRINCIPLES

(75) Inventor: Beng Poon Teng, Gif-sur-Yvette (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 126 days.

(21) Appl. No.: 10/472,408

(22) PCT Filed: Apr. 9, 2002

(86) PCT No.: PCT/FR02/01219

§ 371 (c)(1), (2), (4) Date: Sep. 17, 2003

(87) PCT Pub. No.: WO02/083158

PCT Pub. Date: Oct. 24, 2002

(65) Prior Publication Data

US 2004/0109907 A1 Jun. 10, 2004

(30) Foreign Application Priority Data

Apr. 10, 2001 (FR) .................................. 01 04942

(51) Int. Cl.
*A61K 35/78* (2006.01)
(52) U.S. Cl. ...................... 424/752; 424/776
(58) Field of Classification Search ................ 424/752
See application file for complete search history.

(56) References Cited

U.S. PATENT DOCUMENTS

| | | | | |
|---|---|---|---|---|
| 5,241,084 A | * | 8/1993 | Teng | 549/297 |
| 5,322,688 A | * | 6/1994 | Schwabe | 424/752 |
| 5,389,370 A | * | 2/1995 | O'Reilly et al. | 424/752 |
| 5,599,950 A | * | 2/1997 | Teng | 549/297 |
| 6,030,621 A | * | 2/2000 | De Long et al. | 424/752 |
| 6,328,999 B1 | * | 12/2001 | Schwabe | 424/752 |
| 6,447,819 B1 | * | 9/2002 | Paracchini | 424/752 |
| 6,590,109 B1 | * | 7/2003 | Lichtblau et al. | 549/297 |

FOREIGN PATENT DOCUMENTS

| | | | |
|---|---|---|---|
| CN | 1059825 | * | 12/2000 |
| DE | 3832056 | * | 3/1990 |
| JP | 021193907 | * | 7/1990 |

OTHER PUBLICATIONS

Database WPI, Section Ch, Week 200143, Derwent Publications Ltd., London, GB, An 2001-398915, XP002184929.
Database WPI, Section Ch, Week 199602 Derwent Publications Ltd., London, GB; AN 1996-018388, XP002184930.
Database BIOSIS 'Online!, Biosciences Information Service, Phil., PA, US, Mar. 2000, Koch et al. Evidence . . . Mouse, XP0021841928.

* cited by examiner

*Primary Examiner*—Christopher R. Tate
(74) *Attorney, Agent, or Firm*—Charles A. Muserlian

(57) ABSTRACT

A process for the preparation of an extract of *Ginkgo biloba* leaves, comprising
i. extraction of the dried fragments of *Ginkgo biloba* leaves in ethanol containing a maximum of 20% by weight of water;
ii. concentration of the extract under reduced pressure in the presence of an aqueous solution of sodium chloride and elimination of the dark oil from the remainder of the clear solution;
iii. washing of the residual aqueous solution by liquid-liquid extraction with n-hexane, n-heptane or cyclohexane,
iv. liquid-liquid extraction of the aqueous phase washed with ethyl acetate; and
v. washing of the ethyl acetate phase obtained in stage iv with a sodium chloride solution followed by evaporation to dryness of the washed ethyl acetate phase and use of the resulting extract to treat cerebral and peripheral vascular disorders and neurodegenerative diseases.

10 Claims, 2 Drawing Sheets

METHOD FOR PREPARING AN EXTRACT OF GINKGO BILOBA LEAVES HIGHLY ENRICHED IN ACTIVE PRINCIPLES

This application is a 371 of PCT/FR02/01219 filed Apr. 9, 2002.

The invention relates to a process for the preparation of an extract of *Ginkgo biloba* leaves highly enriched in active ingredients.

Certain standardized phytopharmaceutical preparations based on extracts of *Ginkgo biloba* leaves are currently used to treat cerebral and peripheral vascular disorders, in particular in Europe, the United States and the Far East.

The *Ginkgo biloba* extract most commonly used at present (EGb 761®) contains 24% of flavone-glycosides, 3% of ginkgolides A, B, C and J in total and 3% of bilobalide (cf. K. Drieu, *La Presse Medicale* (1986), 15.1455–1457). The recommended daily dose for a patient is 120 milligrams.

U.S. Pat. No. 5,399,348 describes for example a method for preparing a *Ginkgo biloba* extract with an average composition of 24% of flavone-glycosides, 3% of ginkgolides A, B, C and J and 3% of bilobalide. This method comprises the following stages:

i. extraction of the dried powder of leaves in acetone containing 40% by weight of water;
ii. elimination of the lipids by concentration of the extract under reduced pressure until a concentrate is obtained containing approximately 30% of solids in order to thus eliminate the acetone, then dilution with water in order to obtain a concentration of 15% of solids, cooling down of the suspension obtained to approximately 10° C. for one hour before eliminating the lipid precipitates by filtration;
iii. enrichment of the organic phase by the addition of a 30% ammonium sulphate solution to the aqueous filtrate followed by liquid-liquid extraction with a mixture of methylethylketone and acetone (between 9:1 and 4:6) and concentration of the organic phase in order to obtain a concentration of 50 to 70% solids;
iv. elimination of the tannins by dilution of the concentrate in a 50/50 mixture by weight of water and ethanol in order to obtain a concentration of 10% solids, addition of an aqueous solution of a lead salt until the colour has passed from brown to amber and filtration of the lead-tannin precipitates in order to produce a clear filtrate;
v. elimination of the lead in the form of its insoluble sulphate by concentration of the filtrate in order to keep a maximum proportion of 5% ethanol, addition of ammonium sulphate up to a concentration of approximately 20% followed by liquid-liquid extraction with a mixture of methylethylketone and ethanol (between 8:2 and 1:1); and
vi. drying of the final product by concentration of the organic phase in order to obtain a concentration of 50 to 70% of solids and drying under vacuum in an oven at 60–80° C. in order to isolate the final product containing less than 5% water.

During the last ten years, considerable efforts have been made to enrich the part of the active compounds of *Ginkgo biloba* extracts whilst at the same time reducing the part of the long-chained alkylphenolic allergenic compounds such as the ginkgolic acids.

There are a certain number of patent applications and patents describing processes making it possible to obtain extracts of *Ginkgo biloba* leaves enriched in flavone-glycosides and terpene-lactones.

For example, U.S. Pat. No. 5,389,370 relates to methods for preparing extracts concentrated in active compounds. The strategy used in this case is to mix the fraction rich in flavone-glycosides obtained by liquid-liquid extraction with bilobalide and ginkgolides isolated using column chromatographic separation in order to obtain the desired compositions which typically contain 50% of flavone-glycosides and 6% of bilobalide, 50% of flavone-glycosides and 7% of ginkgolides or 50% of flavone-glycosides, 6% of bilobalide and 7% of ginkgolides. The process described takes up the first two stages of U.S. Pat. No. 5,399,348 mentioned previously (which are here designated as stages 1 and 2) to which the following successive stages are added:

3. enrichment of the organic phases: liquid-liquid extraction with a mixture of ethyl acetate and hexane (9:1), the aqueous phase being re-extracted with n-butanol and the n-butanol phase obtained concentrated to dryness in order to obtain the fraction rich in flavone-glycosides;
4. treatment with activated carbon: washing of the acetate-hexane ethyl phase with water, the washed acetate-hexane ethyl phase then being treated with activated carbon, filtered and concentrated to dryness;
5. recrystallization: dissolution of the solid residue in a 50/50 mixture by weight of ethanol and water, cooling down in order to crystallize and filtration in order to recover the ginkgolides;
6. column chromatography: concentration to dryness of the supernatant of stage 5 and chromatographic separation on a silica gel column in order to obtain fractions rich in bilobalide and ginkgolides; and
7. mixture of fractions: mixture of the fraction rich in flavone-glycosides of stage 3 with the ginkgolides obtained in stage 5 or 6 and/or with the bilobalide obtained in stage 6.

According to a variant of the above process, stages 4 and 5 can be replaced by column chromatography.

Moreover, U.S. Pat. No. 6,030,621 described a method for obtaining *Ginkgo biloba* extracts enriched in flavone-glycosides and in terpene-lactones. The strategy used is analogous to that of U.S. Pat. No. 5,389,370: the fraction rich in flavone-glycosides is mixed with the fractions rich in terpene-lactones, the latter being obtained by column chromatography. Typically, the extracts prepared comprise 47.2% of flavone-glycosides and 6.3% of terpene-lactones or 70% of flavone-glycosides and 10% of terpene-lactones. This method comprises the following stages:

a) extraction of the dried powder of leaves in ethanol containing 50% by weight of water;
b) elimination of the lipids by concentration of the extract under reduced pressure until the ethanol is eliminated, dilution of the concentrate with water, resting the mixture for 48 hours and filtration of the lipid precipitates;
c) trapping of the active compounds by passing the aqueous filtrate through a resin consisting of a mixture of XAD-4 resin (mixture of porous polymers) and polyamide;
d) elution of the active compounds using successive ethanol-water mixtures containing 30, 60 and 90% by weight of ethanol; and
e) combination of all fractions obtained in d), evaporation of the ethanol, washing of the aqueous concentrate with hexane and evaporation to dryness of the washed aqueous phase in order to obtain an extract containing 47.2% of flavone-glycosides and 6.3% of terpene-lactones.

In a variant of the above process, the fraction obtained from the ethanol-water mixture containing 30% of ethanol is subjected to flash chromatography in order to obtain a fraction containing at least 80% of terpene-lactones. In the same fashion, the fractions obtained from the ethanol-water mixtures containing 60 and 90% of ethanol are combined and subjected to flash chromatography in order to obtain a fraction containing at least 80% of flavone-glycosides. The fraction containing at least 80% of flavone-glycosides and the fraction containing at least 80% of terpene-lactones are mixed in different proportions and make it possible to obtain extracts containing up to 70% of flavone-glycosides and 10% of terpene-lactones.

Owing to increasingly stringent health safety requirements, it is becoming preferable to use purer and purer active ingredients. The tendency for *Ginkgo biloba* extracts would therefore be one day to abandon extracts such as the EGb 761® in favour of extracts still richer in active ingredients. Typically, it would be possible to aim at extracts containing at least 50% by weight of flavone-glycosides and 12% by weight of terpene-lactones, or extracts containing at least 30% by weight of terpene-lactones and at least 15% by weight of flavone-glycosides. The processes of U.S. Pat. Nos. 5,389,370 or 6,030,621 would make it possible to obtain such an extract but would however prove to be onerous when used on an industrial scale, chiefly due to the presence of separation stages by chromatography.

The Applicant has just developed a method making it possible to obtain extracts of *Ginkgo biloba* leaves corresponding to the specifications indicated without using any separation stage by chromatography.

A subject of the invention is therefore a process for the preparation of an extract of *Ginkgo biloba* leaves, which comprises the following successive stages:

i. extraction of the dried fragments of *Ginkgo biloba* leaves in ethanol containing a maximum 20% by weight of water;

ii. concentration of the extract under reduced pressure in the presence of an aqueous solution of sodium chloride and elimination of the dark oil from the remainder of the clear solution;

iii. washing of the residual aqueous solution by liquid-liquid extraction with n-hexane, n-heptane or cyclohexane;

iv. liquid-liquid extraction of the aqueous phase washed with ethyl acetate;

v. washing of the ethyl acetate phase obtained in stage iv with a sodium chloride solution then evaporation to dryness of the washed ethyl acetate phase.

By dried fragments of *Ginkgo biloba* leaves, is meant in the present application dry fragments of which the particle size does not exceed 5 mm.

Preferably according to the invention, the dried fragments of *Ginkgo biloba* leaves is in the form of dried powder. By powder, is meant in the present application a powder of which the particle size does not exceed 1 mm (and preferably does not exceed 5 mm).

The process according to the invention can be applied:
either to lyophilized fragments (preferably a powder) of *Ginkgo biloba* leaves, in which case extracts containing at least 50% by weight of flavone-glycosides and 12% by weight of terpene-lactones are obtained;

or to dried fragments (preferably a powder) of *Ginkgo biloba* leaves, in which case extracts—hereafter called "principal extracts"—containing at least 30% by weight of terpene-lactones and at least 15% by weight of flavone-glycosides are obtained (said process in this case making it possible to obtain moreover as a related product of the extracts—hereafter called "related extracts"—analogues to those described in PCT Patent Application WO 96/33728, namely extracts containing approximately 30 to 35% by weight of flavone-glycosides and approximately 1% by weight of terpene-lactones).

According to one of the variants of the invention, the process described above is applied to lyophilized fragments (or a powder) of *Ginkgo biloba* leaves and the extract obtained is preferably such that it contains approximately 52% by weight of flavone-glycosides and approximately 13% by weight of terpene-lactones.

According to the preferred variant of the invention, the process described above is applied to dried fragments (or a powder) of *Ginkgo biloba* leaves and the principal extract obtained is preferably such that it contains from 34 to 46% by weight of terpene-lactones and from 18 to 30% by weight of flavone-glycosides. More preferentially, the process described above is applied to dried fragments (or a powder) of *Ginkgo biloba* leaves the principal extract obtained is such as it contains of 36 to 44% by weight of terpene-lactones and of 18 to 30% by weight of flavone-glycosides. In particular, the process described above is applied to dried fragments (or a powder) of *Ginkgo biloba* leaves and the principal extract obtained will contain approximately 40% by weight of terpene-lactones (of which approximately 24.5% by weight of ginkgolides A, B and C and approximately 15.5% by weight of bilobalide) and approximately 24% by weight of flavone-glycosides.

Preferably, the extraction of stage i is carried out using ethanol containing between 10 and 20% by weight of water, and more preferentially between 15% and 20% by weight of water.

Preferably also, the mixture obtained after concentration of the extract under reduced pressure in the presence of an aqueous solution of sodium chloride during stage ii is cooled down, for example to a temperature of approximately 10° C., preferably for a duration from 10 or 15 minutes to 1 or 2 hours, before carrying out elimination of the dark oil from the remainder of the clear solution. Yet more preferably, celite is added to the mixture obtained after concentration of the extract under reduced pressure in the presence of an aqueous solution of sodium chloride during stage ii and the whole of the ethanol present in said mixture is evaporated before cooling down said mixture.

Preferably also, the washing of stage iii is carried out with n-heptane.

According to a particularly preferred variant of the process of the invention when the latter is applied to dried fragments (or a powder) of *Ginkgo biloba* leaves, the volume of the residual aqueous solution washed in stage iii and the quantity of sodium chloride in the solution are adjusted beforehand so that, on the one hand, the content by weight of water-soluble solids i.e. approximately 8% with respect to the total weight of the solution, and on the other hand, the content by weight of sodium chloride i.e. 16% with respect to the total weight of the solution. The content of water-soluble solids is evaluated by taking a sample of ethanolic solution which is evaporated to eliminate the ethanol then extracted with dichloromethane, the residual aqueous phase then being evaporated to dryness and weighed; the content of water-soluble solids can then be deduced from the mass of solid residue obtained.

As regards stage iv, methylethylketone containing 2 to 10% of acetone or ethanol by volume could optionally replace the ethyl acetate.

As regards to the aqueous solutions of sodium chloride used in stages ii and v, these will preferably have a concentration of at least 10% by weight of sodium chloride, whilst they will preferably be saturated in sodium chloride for stage v.

According to a preferred variant of the above process applied to dried fragments (or a powder) of *Ginkgo biloba* leaves, the saline aqueous phase recovered at the end of the liquid-liquid extraction of stage iv can be retreated by a process comprising the following stages:

a) liquid-liquid extraction using an approximately 1:1 mixture of ethyl acetate and ethanol; and
b) evaporation to dryness of the organic phase recovered at the end of stage a);
c) dissolution of the residue obtained in stage b) in absolute ethanol in order to have a concentration of approximately 5% to 10% by weight of solids with respect to the mass of the ethanol solution;
d) cooling down of the mixture to a temperature preferably below or equal to 10° C. (for example to a temperature of 2 to 8° C.), preferably for a duration of 30 minutes to 12 hours;
e) filtration and evaporation of the ethanol of the filtrate recovered in order to produce a dry extract.

This additional process makes it possible to recover an additional extract, which generally contains approximately 30 to 35% by weight of flavone-glycosides and approximately 1% by weight of terpene-lactones.

Optionally, the process described above can comprise, after stages i to v, the following stage vi:

vi. solubilization of the dry extract in ethanol and cooling down the solution to a temperature preferably below or equal to 10° C. (for example to a temperature of 2 to 8° C.), filtration of the optionally precipitated salt and evaporation to dryness of the resultant solution.

In this case, when the process of the invention is used on an industrial scale, it is preferable that stage v simply concentrates the organic phase until a concentration of about 50 to 70% by weight of solids is obtained (and not evaporate it to dryness) and adding ethanol in order to have a composition containing 5 to 20% by weight of water, 5 to 20% by weight of solids and the remainder ethanol before carrying out stage vi. By proceeding in this way a drying stage is saved.

The principal extracts obtained according to the invention can be used in pharmacy or in the food sector (for example as ingredients of nutritional supplements) as, on the one hand, they contain less than 5 ppm of alkylphenols (measurement carried out by HPLC assay) and, on the other hand, they contain less than 0.3% of prodelphinidines (preferably less than 0.25% and generally between 0.05 and 0.25% of prodelphinidines). Moreover, they also contain few lipophilic impurities and few polysaccharides, proanthocyanidines other than prodelphinidines and proteins with a high molecular mass.

In particular, owing to their low prodelphinidine content, the principal extracts according to the invention are better suited to administration to patients by intravenous route. By way of comparison, a commercial extract such as EGb 761® can contain up to 1.5% of prodelphinidines.

In addition, the principal extracts of the invention are preferably such that the peaks corresponding to O-rhamnopyranosyl-4-O-D-(trans-p-coumaroyl- 6'")glucopyranosyloxy-3-tetrahydroxy-3',4',5,7-flavonol (or quercetin 3-(6'''-trans-p-coumaroyl)-glucorhamnoside) O-rhamnopyranosyl-4-O-D-(trans-p-coumaroyl-6''')glucopyranosyloxy-3-trihydroxy-4'5,7-flavonol (or kaempferol 3-(6'''-trans-p-coumaroyl)-glucorhamnoside) together represent approximately 39% of the total surface of the peaks of the chromatogram. In particular, the principal extracts of the invention will be preferably such that the peak corresponding to O-rhamnopyranosyl-4-O-D-(trans-p-coumaroyl-6''') glucopyranosyloxy-3-tetrahydroxy-3',4',5,7-flavonol (or quercetin 3-(6'''-trans-p-coumaroyl)-glucorhamnoside) represents approximately 20% of the total surface of the peaks of the chromatogram. Similarly, the principal extracts of the invention will be preferably such that the peak corresponding to O-rhamnopyranosyl-4-O-D-(trans-p-coumaroyl-6''') glucopyranosyloxy-3-trihydroxy-4'5,7-flavonol (or kaempferol 3-(6'''-trans-p-coumaroyl)-glucorhamnoside) represents approximately 19% of the total surface of the peaks of the chromatogram.

Moreover, the related extracts obtained using the process according to the invention will contain less than 0.5% of prodelphinidines (preferably less than 0.40% and generally between 0.15 and 0.40% of prodelphinidines).

A further subject of the invention is the principal extracts which can be obtained by a process according to the invention. A subject of the invention is also said principal extracts as medicaments, the pharmaceutical compositions comprising said principal extracts as active ingredient and the use of said principal extracts for preparing medicaments intended to treat diseases/disorders chosen from the following diseases/disorders: cerebral and peripheral vascular disorders (such as tinnitus of vascular origin, atherosclerosis, ischemia, thromboses, symptoms related to venous insufficiency, acute inflammatory venous manifestations and symptoms related to a hemorrhoidal crisis), neurodegenerative diseases (such as for example Alzheimer's disease, Parkinson's disease, Huntington's chorea or amyotrophic lateral sclerosis) and chronic neurosensory and cognitive pathological deficit in the aged (in particular the memory loss observed in the aged patient who is not suffering from Alzheimer's disease or other dementia). Finally a subject of the invention is the use of said principal extracts for preparing medicaments intended to offer an adjuvant therapy for treating proliferative diseases (in particular cancer).

The pharmaceutical compositions containing an extract of the invention can be in solid form such as, for example, powders, pills, granules, tablets, liposomes, gelatin capsules or suppositories. The pills, tablets or gelatin capsules can be coated with a substance capable of protecting the composition from the action of gastric acid or enzymes in the stomach of the subject for a sufficient period of time to allow this composition to pass undigested into the latter's small intestine. The extract can also be administered locally, for example to the actual site of a tumour. The extract can also be administered according to a sustained release process (for example using a sustained release composition or a perfusion pump). Appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax.

The pharmaceutical compositions containing an extract of the invention can also be presented in liquid form such as, for example, solutions, emulsions, suspensions or a sustained release formulation. Appropriate liquid supports can be, for example, water, organic solvents such as glycerol or the glycols such as polyethylene glycol, similarly their mixtures, in varying proportions, in water.

The administration of a medicament according to the invention can be carried out by topical, oral, parenteral route, by intramuscular injection, etc.

The dose of an extract according to the present invention, provided for the treatment of the diseases or disorders mentioned above, varies according to the administration method, the age and body weight of the subject to be treated as well as the state of the latter, and is finally decided by the attending doctor or vet. Such a quantity determined by the attending doctor or vet is here called "therapeutically effective quantity".

Without prejudging the opinion of the attending doctor, and given the content of active ingredients of the principal extracts according to the invention, the administration to a human being of a daily dose of 5 to 150 mg, and preferably of a dose of 10 to 100 mg (in particular a dose of 40 to 80 mg, for example of 50 to 70 mg) of said principal extracts can for example be envisaged.

In the present Application, the term "approximately" refers to an interval around the value considered. As used in the present Application, "approximately X" signifies an interval of X minus 10% of X to X plus 10% of X, and preferably an interval of X minus 5% of X to X plus 5% of X.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The examples which follow are presented in order to illustrate the above processes and should in no event be considered as a limit to the scope of the invention.

EXAMPLES

Example 1

100 g of lyophilized ground *Ginkgo biloba* leaves (particle size less than 4 mm) are extracted twice, once with 800 ml and a second time with 600 ml of an ethanol-water mixture containing 88% by weight of ethanol, each time at 60° C. and for 1 hour. The extracts of the two extraction stages are filtered and the remains of the leaves are recovered and rinsed with 200 ml of the same mixture of solvents. The combined extracts are reduced by evaporation to a volume of 100 ml with a solid product content of approximately 35 g. 350 ml of an aqueous solution of sodium chloride at 10% by weight is added to the ethanolic concentrate and evaporation is continued under reduced pressure at 50° C. in order to eliminate the remaining ethanol. The light orange limpid saline solution is separated from the dark oil by decantation through a cotton wool ball in a filtering funnel then by filtration through celite with suction. The extract in aqueous saline solution is washed with two portions of 150 ml of n-heptane before being extracted twice with 150 ml of ethyl acetate each time. The combined ethyl acetate phases are washed with 50 ml of a saturated solution of sodium chloride then evaporated to dryness under reduced pressure. The dry extract is redissolved in 60 ml of absolute ethanol, left overnight in a refrigerator at 5° C., filtered in order to eliminate the optionally precipitated salt and the filtrate is evaporated to dryness in order to produce 1.42 g of extract containing 51.7% of flavone-glycosides and 13% of terpene-lactones (6.55% of bilobalide).

Example 2

100 g of *Ginkgo biloba* leaves obtained after drying in an industrial rotary oven and ground (particle size less than 4 mm; content 1.8% by weight of flavone glycosides and 0.12% by weight of ginkgolides) are extracted twice, once with 800 ml and a second time with 600 ml of an ethanol-water mixture containing 80% by weight of ethanol, each time at 60° C. and for 1 hour. The extracts of the two extraction stages are filtered and the remains of the leaves are recovered and rinsed with 200 ml of the same mixture of solvents. The combined extracts are reduced by evaporation to a volume of 800 ml with a solid product content of approximately 33 g. 60 g of sodium chloride, 100 ml of water and 22 g of celite are added to the ethanolic concentrate and evaporation is continued under reduced pressure at 50° C. in order to eliminate the remaining ethanol.

The aqueous concentrate is cooled down to 10° C. for one hour and the light orange limpid saline solution is separated from the dark oil by decantation through a cotton wool ball in a filtering funnel, then by filtration with suction on frit covered by a bed of celite. The extract in aqueous saline solution (~300 ml) is washed with two portions of 125 ml of n-heptane before being extracted twice with 125 ml of ethyl acetate each time. The combined ethyl acetate phases are washed with 50 ml of a saturated solution of sodium chloride then evaporated to dryness under reduced pressure. The dry extract is redissolved in 23 ml of absolute ethanol, left overnight in a refrigerator at 4° C., filtered in order to eliminate the optionally precipitated salt and the filtrate is evaporated to dryness in order to produce 1.06 g of extract containing 23.6% of flavone-glycosides, 39.2% of terpene-lactones (including 24.6% of ginkgolides A, B and C and 14.5% of bilobalide) and approximately 0.14% of prodelphinidines.

Example 3

The aqueous phase saline which is recovered after the successive stages of washing with n-heptane and extraction with ethyl acetate of the process for the preparation of the extract of Example 2 is subjected to liquid-liquid extraction using two portions of 125 ml of a ethyl acetate-ethanol mixture 1:1. The organic phase recovered is evaporated to dryness. The dry extract is taken up in absolute ethanol in order to have a concentration of 5% by weight of dry extract with respect to the total weight of the solution. The mixture is left overnight in a refrigerator at 4° C. before being filtered on paper (the solids are rinsed with absolute ethanol at 4° C.). After evaporation to dryness, an extract is obtained containing 31.88% of flavone-glycosides and 0.67% of terpenes (including 0.50% of ginkgolides A, B and C and 0.17% of bilobalide) and approximately 0.21% of prodelphinidines.

Characterization of the Extracts According to the Invention

A) HPLC:

The extracts according to the invention can be characterized using the High Performance Liquid Chromatography method (HPLC) with the elution gradients described hereafter.

Equipment

Liquid phase chromatograph and equipment adapted to the conditions specified hereafter Laboratory glassware Balance accurate to 0.1 mg.

Reagents

Pure water (HPLC quality)

Acetonitrile (HPLC quality)

Isopropanol (HPLC quality)
Acid citric (HPLC quality)
Methanol R
Reference standard *Ginkgo biloba* extract Procedure A solution of the extract to be tested is prepared by dissolving 200 mg of extract to be analyzed in 10 ml of methanol. In parallel, 200 mg of reference standard *Ginkgo biloba* extract (EGb 761®) are dissolved in 10 ml of methanol and constitute the reference solution.

The following chromatography conditions are used:

| | | |
|---|---|---|
| Type of gradient: | linear from 0% to 100% of secondary mobile phase for 15 minutes then 5 minutes with the secondary mobile phase. Re-equilibrate the column for 10 minutes with the primary mobile phase before the following injection. | |
| Primary mobile phase: | purified water | 1000 ml |
| | acetonitrile | 200 ml |
| | isopropanol | 30 ml |
| | citric acid | 4.92 g |
| Secondary mobile phase: | purified water | 1000 ml |
| | acetonitrile | 470 ml |
| | isopropanol | 50 ml |
| | citric acid | 6.08 g |
| Flow rate: | 1.5 ml/minute | |
| Detection: | UV 360 nm | |
| Column: | Stainless steel, 15 cm, diameter 4.6 mm; filled with silica gel for chromatography Macherey-Nagel R Nucleosil 5C18 or equivalent (5 µm). | |
| Volume injected: | 5 µl | |

Results

BRIEF DESCRIPTION OF THE DRAWINGS

The chromatogram obtained for the extract obtained in Example 2 is reproduced in FIG. 1 and that for the extract obtained in Example 3 in FIG. 2.

The integrations determined for the different peaks are reproduced in Tables I (extract of Example 2) and II (extract of Example 3) hereafter. The major peaks having a retention time of approximately 13 to 15 minutes under the conditions described above corresponding respectively to O-rhamnopyranosyl-4-O-D-(trans-p-coumaroyl-6''')glucopyranosyloxy-3-tetrahydroxy-3',4',5,7-flavonol (or quercetin 3-(6'''-trans-p-coumaroyl)-glucorharmnoside) and to O-rhamnopyranosyl-4-O-D-(trans-p-coumaroyl-6''')glucopyranosyloxy-3-trihydroxy-4'5,7-flavonol (or kaempferol 3-(6'''-trans-p-coumaroyl)-glucorhamnoside).

TABLE I

Figure 1:
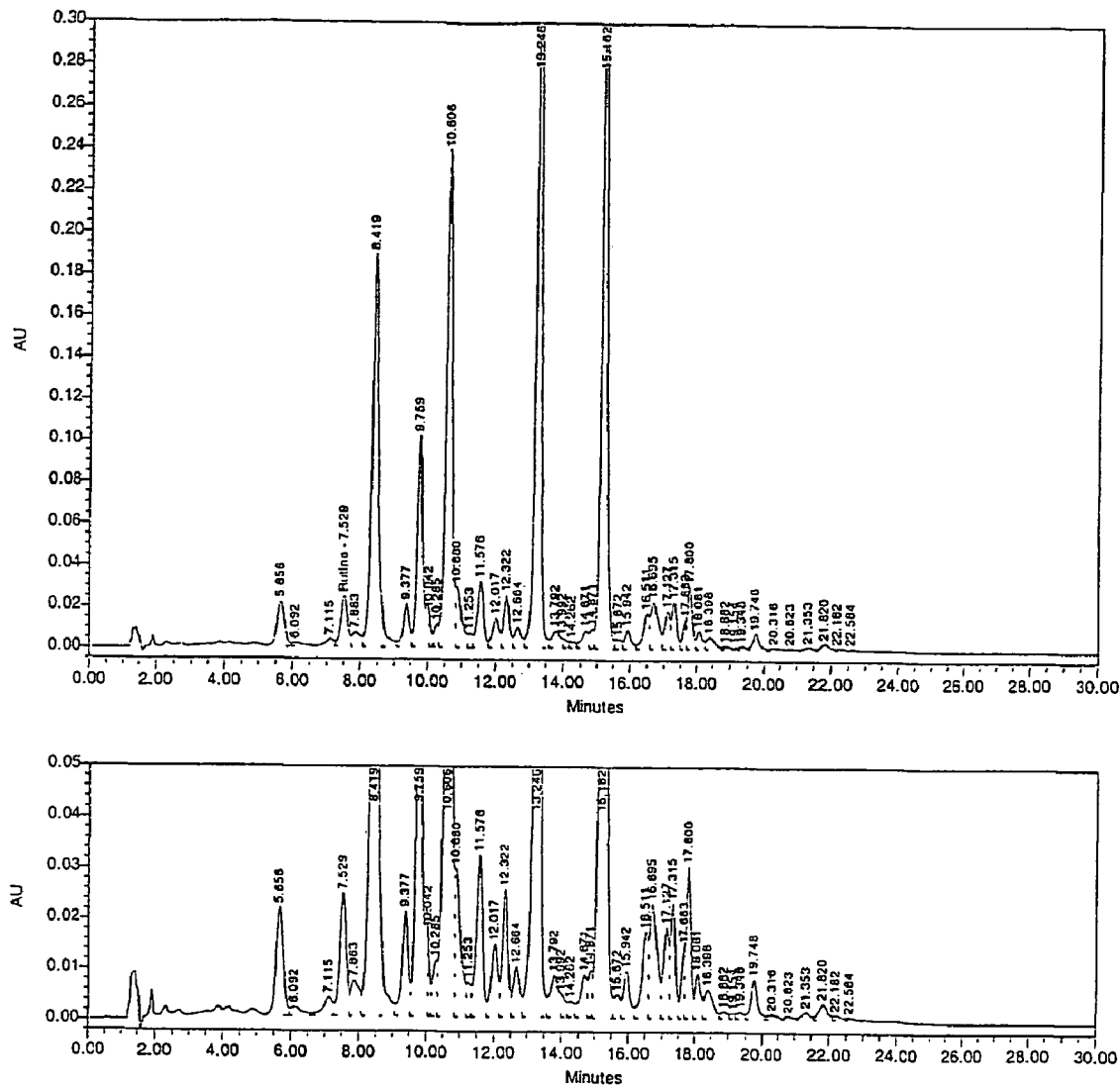
Figure 2:
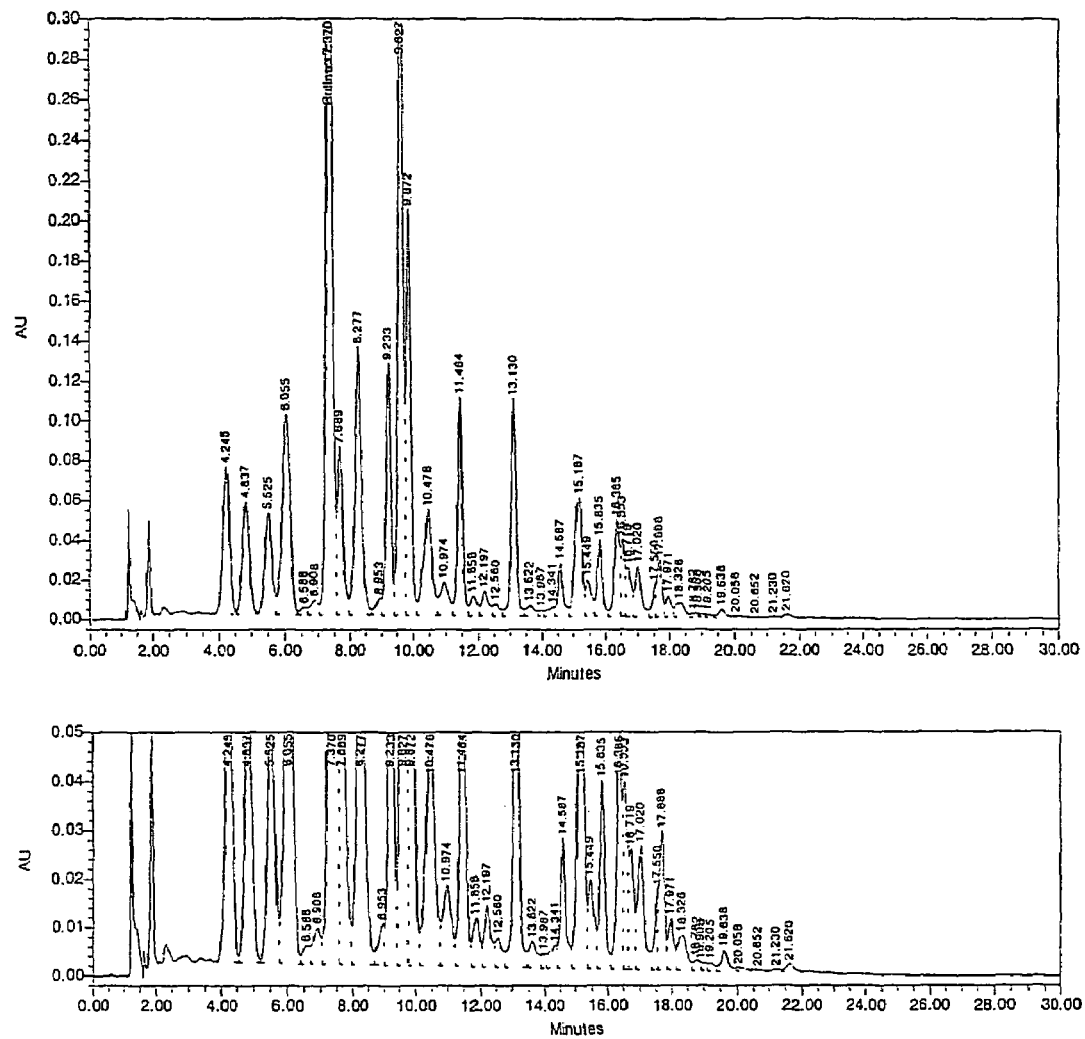

| Peak no. | R.T. (minutes) | Integration type | Surface | % surface |
|---|---|---|---|---|
| 1 | 5.66 | BV | 323169.34 | 1.63 |
| 2 | 6.09 | VV | 40920.21 | 0.21 |
| 3 | 7.12 | VV | 69832.25 | 0.35 |
| 4 | 7.53 | VV | 335574.32 | 1.69 |
| 5 | 7.86 | VV | 119797.71 | 0.60 |
| 6 | 8.42 | VV | 2633527.95 | 13.25 |
| 7 | 9.38 | VV | 272916.32 | 1.37 |
| 8 | 9.76 | VV | 1226466.81 | 6.17 |
| 9 | 10.04 | VV | 72124.84 | 0.36 |
| 10 | 10.29 | Vv | 97259.69 | 0.49 |
| 11 | 10.61 | vv | 2967432.21 | 14.93 |
| 12 | 10.88 | vV | 343065.16 | 1.73 |
| 13 | 11.25 | VV | 61980.66 | 0.31 |
| 14 | 11.58 | VV | 405705.79 | 2.04 |
| 15 | 12.02 | VV | 193158.96 | 0.97 |

TABLE I-continued

| Peak no. | R.T. (minutes) | Integration type | Surface | % surface |
|---|---|---|---|---|
| 16 | 12.32 | VV | 295426.85 | 1.49 |
| 17 | 12.66 | VV | 139571.25 | 0.70 |
| 18 | 13.25 | VV | 39600621.99 | 19.93 |
| 19 | 13.79 | Vv | 145778.77 | 0.73 |
| 20 | 13.99 | vV | 38952.25 | 0.20 |
| 21 | 14.26 | VV | 39634.91 | 0.20 |
| 22 | 14.67 | VV | 119350.40 | 0.60 |
| 23 | 14.87 | VV | 85122.51 | 0.43 |
| 24 | 15.18 | VV | 3789171.34 | 19.07 |
| 25 | 15.67 | VV | 60575.37 | 0.30 |
| 26 | 15.94 | VV | 118616.10 | 0.60 |
| 27 | 16.51 | VV | 208977.01 | 1.05 |
| 28 | 16.69 | VV | 345205.90 | 1.74 |
| 29 | 17.13 | VV | 206765.44 | 1.04 |
| 30 | 17.32 | VV | 241246.27 | 1.21 |
| 31 | 17.68 | Vv | 95087.16 | 0.48 |
| 32 | 17.80 | vV | 311413.97 | 1.57 |
| 33 | 18.08 | VV | 108167.40 | 0.54 |
| 34 | 18.40 | VV | 103158.38 | 0.52 |
| 35 | 18.88 | VV | 19884.37 | 0.10 |
| 36 | 19.15 | VV | 9701.13 | 0.05 |
| 37 | 19.35 | VV | 18389.23 | 0.09 |
| 38 | 19.75 | VV | 109237.26 | 0.55 |
| 39 | 20.42 | VV | 21754.52 | 0.11 |
| 40 | 20.82 | VV | 13348.93 | 0.07 |
| 41 | 21.35 | VV | 26491.23 | 0.13 |
| 42 | 21.82 | VV | 55867.45 | 0.28 |
| 43 | 22.18 | VV | 14634.07 | 0.07 |
| 44 | 22.58 | VB | 7095.01 | 0.04 |
| TOTAL | | | 19872178.50 | |

TABLE II

| Peak no. | R.T. (minutes) | Integration type | Surface | % surface |
|---|---|---|---|---|
| 1 | 4.25 | BV | 1082912.49 | 3.74 |
| 2 | 4.84 | VV | 853793.45 | 2.95 |
| 3 | 5.52 | VV | 767098.18 | 2.65 |
| 4 | 6.06 | VV | 1634400.29 | 5.68 |
| 5 | 6.59 | VV | 53647.35 | 0.19 |
| 6 | 6.91 | VV | 127266.30 | 0.44 |
| 7 | 7.37 | VV | 5275614.83 | 18.22 |
| 8 | 7.69 | VV | 1062334.77 | 3.67 |
| 9 | 8.28 | VV | 1918663.93 | 6.63 |
| 10 | 8.95 | Vv | 103523.93 | 0.36 |
| 11 | 9.23 | vV | 1390204.37 | 4.80 |
| 12 | 9.63 | VV | 3866788.04 | 13.35 |
| 13 | 9.87 | VV | 2102182.30 | 7.26 |
| 14 | 10.48 | VV | 968935.87 | 3.35 |
| 15 | 10.97 | VV | 314304.16 | 1.0 |
| 16 | 11.46 | VV | 1167341.28 | 4.03 |
| 17 | 11.86 | VV | 143179.61 | 0.49 |
| 18 | 12.20 | VV | 193515.76 | 0.67 |
| 19 | 12.56 | Vv | 91823.99 | 0.32 |
| 20 | 13.13 | vV | 1197144.99 | 4.13 |
| 21 | 13.62 | VV | 94540.18 | 0.33 |
| 22 | 13.99 | VV | 33698.24 | 0.12 |
| 23 | 14.34 | VV | 78763.83 | 0.27 |
| 24 | 14.59 | VV | 334542.58 | 1.16 |
| 25 | 15.19 | VV | 944041.64 | 3.26 |
| 26 | 15.45 | VV | 244838.93 | 0.85 |
| 27 | 15.84 | VV | 473019.80 | 1.51 |
| 28 | 16.39 | VV | 569694.64 | 1.97 |
| 29 | 16.55 | Vv | 323620.29 | 1.12 |
| 30 | 16.72 | vV | 255311.37 | 0.88 |
| 31 | 17.02 | VV | 370249.91 | 1.28 |
| 32 | 17.55 | Vv | 106207.91 | 0.37 |
| 33 | 17.69 | vV | 338307.55 | 1.17 |
| 34 | 17.97 | VV | 134115.60 | 0.46 |
| 35 | 18.33 | VV | 148609.32 | 0.51 |
| 36 | 18.78 | Vv | 31564.17 | 0.11 |
| 37 | 18.91 | vV | 17047.61 | 0.06 |
| 38 | 19.20 | VV | 25147.79 | 0.09 |
| 39 | 19.64 | VV | 67214.23 | 0.23 |

TABLE II-continued

| Peak no. | R.T. (minutes) | Integration type | Surface | % surface |
|---|---|---|---|---|
| 40 | 20.06 | VV | 16329.48 | 0.06 |
| 41 | 20.65 | VV | 11266.06 | 0.04 |
| 42 | 21.23 | VV | 10502.29 | 0.04 |
| 43 | 21.62 | VV | 40624.23 | 0.14 |
| TOTAL | | | 28956906.57 | |

B) Determination of the Prodelphinidine Content:

The prodelphinidine content of the extracts of the invention is evaluated as disclosed hereafter.

Approximately 50 mg of extract are dissolved in 25 ml of a mixture of isopropanol and 3N hydrochloric acid solution (5/1 v/v). 5 ml of the mixture obtained are transferred to a 10 ml flask sealed by a liquid-tight stopper and the flask is then immersed in boiling water for 45 minutes. After cooling down to 20° C., the volume is increased to 10 ml by adding the mixture of isopropanol and 3N hydrochloric acid solution. The absorbance is measured at 556 nm and the percentage of prodelphinidines is obtained by carrying out the following calculation:

% prodelphinidines=$A \times 86.206897/B$

A: absorbance at 556 nm

B: mg of sample

In order to reduce uncertainty as to the result, the experiment is repeated 3 times and an average is calculated from the results obtained.

Pharmacological Properties of the Extracts According to the Invention

In order to demonstrate the pharmacological properties of extracts according to the invention, the following tests can be carried out.

1) Cell Proliferation

Cell Lines

MDA-231 breast cancer cell lines were acquired from the Lombardi Cancer Center (Georgetown University Medical Center). These cell lines are cultured in polystyrene culture dishes (Corning) and multiplied in Dulbecco's modified Eagle medium (DMEM) supplemented with 10% of foetal bovine serum (FBS).

Binding Tests

The MDA-231 cells are dispersed by trituration in 5 ml of phosphate buffered saline solution (PBSS) then centrifuged at 500 g for 15 minutes. The centrifuged cells are resuspended in a PBSS and tested in order to measure their protein content. [$^3$H]PK 11195 tests can be carried out as described in Papadopoulos et al., *J. Biol. Chem.* (1990), 265, 3772–3779 and Hardwick et al., *Cancer Res.* (1999), 59, 831–842. The [N-methyl-$^3$H]PK 11195 or (1-(2-chlorophenyl)-N-methyl-N-(1-methyl-propyl)-3-isoquinolinecarboxamide is obtained from Du Pont-New England Nuclear (Wilmington, Del. USA) and the PK 11195 from Research Biochemicals Incorporated (Natick, Mass. USA). The results obtained are analyzed using the program LIGAND (Munson and Robard, *Anal. Biochem.* (1976), 72, 248–254.

Northern RNA Analysis

The expression of the mRNA of peripheral type benzodiazepine receptors (PBR) in MDA-231 cells treated with the extract of Example 1 or Example 2 or EGb 761® (reference) can be evaluated using a Northern analysis as described in Hardwick et al., *Cancer Res.* (1999), 59, 831–842. The total cellular RNA was isolated using the reagent RNAzol B (TEL-TEST, Inc., Friendswood, Tex. USA) and chloroform. 20 μg of total RNA is passed over 1% agarose gel and transferred overnight onto nylon membranes (S&S Nytran, Scheicher & Schuell, Keene, N.H. USA). A human cDNA fragment of PBR 0.2 kb in length (derived from the pCMV5-PBR plasmid vector containing the complete sequence of human PBR) is labelled using [α-$^{32}$P] dCTP using a random identification system of DNA primers (Life Technologies, Gaithersburg, Md. USA). The hybridization conditions used are described in the reference mentioned previously. The autoradiography is carried out by exposing the blots to an X-OMAT AR film (Kodak, Rochester, N.Y. USA) at −70° C. for 4–48 hours. Quantification of PBR mRNA is carried out using the SigmaGel software (Jandel Scientific, San Rafel, Calif. USA).

Cell Proliferation

MDA-231 cells are placed on 96-well plates (Corning, N.J. USA) at a concentration of approximately 10,000 cells per well (incubation for 24 hours) or 5,000 cells per well (incubation for 48 hours) in DMEM supplemented with 0.1% of FBS. The cells are then incubated in 10% FBS with varying concentrations of the compound of the example or reference compound (EGb 761®) for the periods indicated above. The differences in terms of cell proliferation are analyzed by measuring the quantity of 5-bromo-2'-deoxyuridine (BrdU) incorporated, which is determined by using ELISA BrdU equipment (Boehringer Mannheim, Indianapolis, Ind. USA). The incorporation of BrdU is measured at the wavelength of 450 nm (reference: 690 nm).

2) Glutamate-induced Neurotoxicity

An extract according to the invention can be tested as follows: rat brain neurons are treated or not treated with increasing concentrations of extract of Example 1 or Example 2 above, then, 30 minutes later, are exposed to glutamate at a concentration of 250 μM. The dose inhibiting 50% of the toxicity of the glutamate (designated by $IC_{50}$) can then be evaluated then compared to that obtained for an extract such as EGb 761®, less rich in flavone-glycosides and terpene-lactones (namely 100 μg of EGb 761® per ml).

3) Cell Toxicity

The effects of an extract according to the invention on the viability of the cells can be studied on an HT 22 cell line (mouse hippocampal cells). The viability of the cells is estimated by determination of the quantity of LDH released by cells treated with increasing doses of the extract of Example 1 or Example 2 above and by the Trypan blue exclusion test.

Cell Lines

The HT-22 cell line originates from the Salk Institute for Biological Research (La Jolla, Calif., USA). This cell line is maintained at 37° C. in Dulbecco's modified Eagle medium (DMEM) supplemented with 10% of foetal bovine serum (FBS), hereafter called complete medium.

Test Protocol

HT-22 cells are placed on a 96-well plate at a concentration of $5.10^3$ cells per well in the complete medium. 24 hours later, the extract of the example is solubilized in DMEM and added at a concentration of 10, 25, 50, 100, 250, 500 and 1000 μg/ml; the extract is then left in contact for 24 or 48 hours. The LDH measurement is carried out using a Promega assay kit according to the instructions provided by the manufacturer. The absorbancies are read at 470 nm. The maximum LDH release is obtained after complete lysis of the cells using Triton X-100.

For the viability measurements estimated by the Trypan blue exclusion test, the cells are placed in 6-well plates and the extract of Example 1 or Example 2 is added at a concentration of 100 μg/ml over 24 hours.

The cells are then washed with a phosphate buffer solution free from calcium and magnesium and exposed to trypsin for 5 minutes at 37° C. The reaction is stopped with complete medium and 0.04% of trypan blue is added to the cell suspension. The number of cells which exclude the stain (i.e. the living cells) is determined using a hematocytometer. The cell viability percentage is calculated as follows: number of viable cells (not stained)/total number of cells (stained and not stained)×100.

The invention claimed is:

1. A process for the preparation of an extract of *Ginkgo biloba* leaves, comprising:
   i. extraction of dried fragments of *Ginkgo biloba* leaves in the form of dried powder in ethanol containing a maximum of 20% by weight of water;
   ii. concentration of the extract under reduced pressure in the presence of an aqueous solution of sodium chloride and elimination of the dark oil from the remainder of the clear solution;
   iii. washing of the residual aqueous solution by liquid-liquid extraction with a member selected from the group consisting of n-hexane, n-heptane and cyclohexane;
   iv. liquid-liquid extraction of the washed aqueous phase with ethyl acetate; and
   v. washing of the ethyl acetate phase obtained in stage iv with a sodium chloride solution followed by evaporation to dryness of the washed ethyl acetate phase.

2. The process of claim 1, wherein it includes no chromatographic stage.

3. The process of claim 1 wherein the extraction of stage i is carried out using ethanol containing from 10 to 20% by weight of water.

4. The process of claim 1 wherein the washing of stage iii is carried out with n-heptane.

5. The process of claim 1 wherein the aqueous solutions of sodium chloride used in stages ii and v have a concentration of at least 10% by weight of sodium chloride.

6. The process of claim 1 wherein, after stages i to v, the following stage is effected:
   vi. solubilization of the dry extract in ethanol and cooling down the solution, filtration of the optionally precipitated salt and evaporation to dryness of the resultant solution.

7. An extract of *Ginkgo biloba* leaves obtained by the process of claim 1 wherein the extract contains from 34 to 46% by weight of terpene-lactones and from 18 to 30% by weight of flavone-glycosides.

8. A pharmaceutical composition comprising an extract of claim 7 and an inert pharmaceutical carrier.

9. A method of treating cerebral and peripheral vascular disorders and neurodegenerative diseases in warm-blooded animals comprising administering to warm-blooded animals in need thereof an amount of the extract of claim 7 sufficient to treat the same.

10. A method of treating proliferative diseases in warm-blooded animals comprising administering to warm-blooded animals in need thereof an amount of the extract of claim 7 as an adjuvant therapy.

* * * * *